United States Patent [19]

Greenfield

[11] Patent Number: 5,529,074
[45] Date of Patent: Jun. 25, 1996

[54] UNIFORM PRESSURE DIAGNOSTIC PINWHEEL

[76] Inventor: Jon B. Greenfield, 436 N. Roxbury Dr., #202, Beverly Hills, Calif. 90210

[21] Appl. No.: 454,957

[22] Filed: May 31, 1995

Related U.S. Application Data

[63] Continuation-in-part of Ser. No. 23,593, Feb. 26, 1993, Pat. No. 5,433,212.

[51] Int. Cl.⁶ .................................................. A61B 19/00
[52] U.S. Cl. ............................................................. 128/744
[58] Field of Search ............................ 128/740, 744, 128/774

[56] References Cited

U.S. PATENT DOCUMENTS

| | | | |
|---|---|---|---|
| 3,074,395 | 1/1963 | Kevorkian | 128/744 |
| 3,344,781 | 10/1967 | Allen | 128/744 |
| 3,515,125 | 6/1970 | Ruskin | 128/744 |
| 4,823,806 | 4/1989 | Bajade | 128/744 |
| 5,222,504 | 6/1993 | Soloman | 128/744 |

FOREIGN PATENT DOCUMENTS

| | | | |
|---|---|---|---|
| 1297807 | 6/1969 | Germany | 128/744 |

*Primary Examiner*—Max Hindenburg
*Attorney, Agent, or Firm*—Marvin H. Kleinberg; Marshall A. Lerner; Michael J. Ram

[57] ABSTRACT

A disposable diagnostic pinwheel for use in testing for nerve dysfunction. The pinwheel can be applied to a handle which incorporates a pressure absorbing mechanism so that a more constant and controllable test can be conducted. The pinwheel can also include a removable cover which protects sharp points on the pinwheel from inadvertently injuring the user. In one embodiment the cover may also function as the grasping means during use of the pinwheel in testing procedures. In such a use the cover also includes the pressure absorbing mechanism.

17 Claims, 5 Drawing Sheets

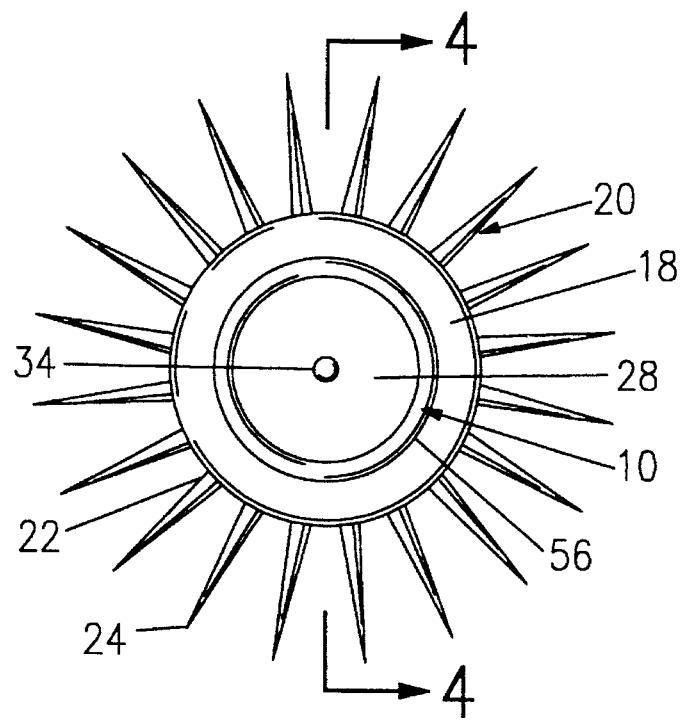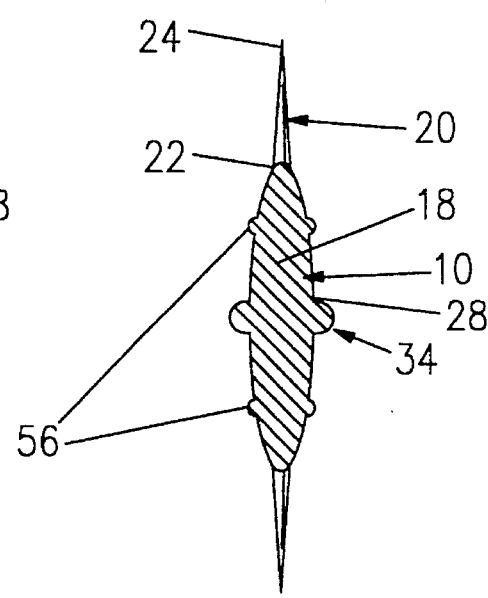
fig. 3    fig. 4
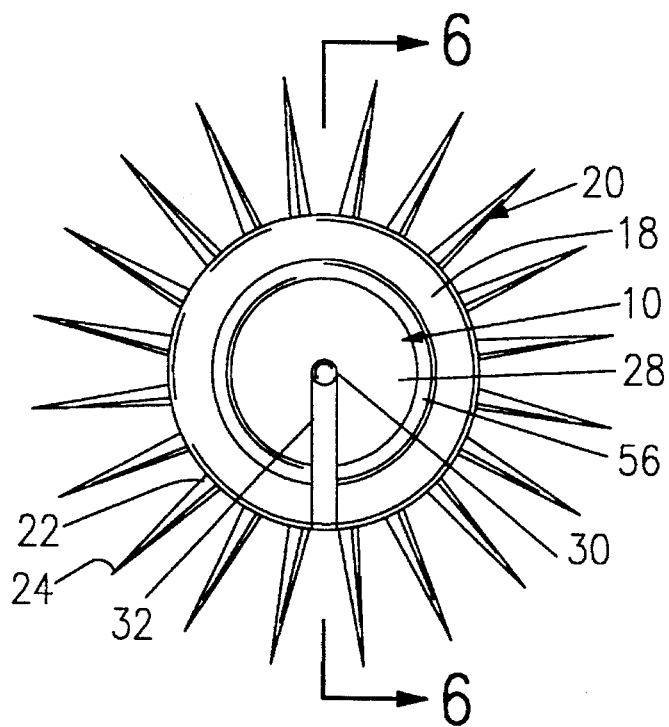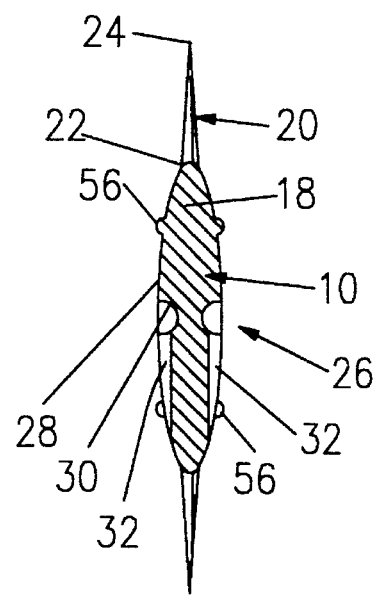
fig. 5    fig. 6

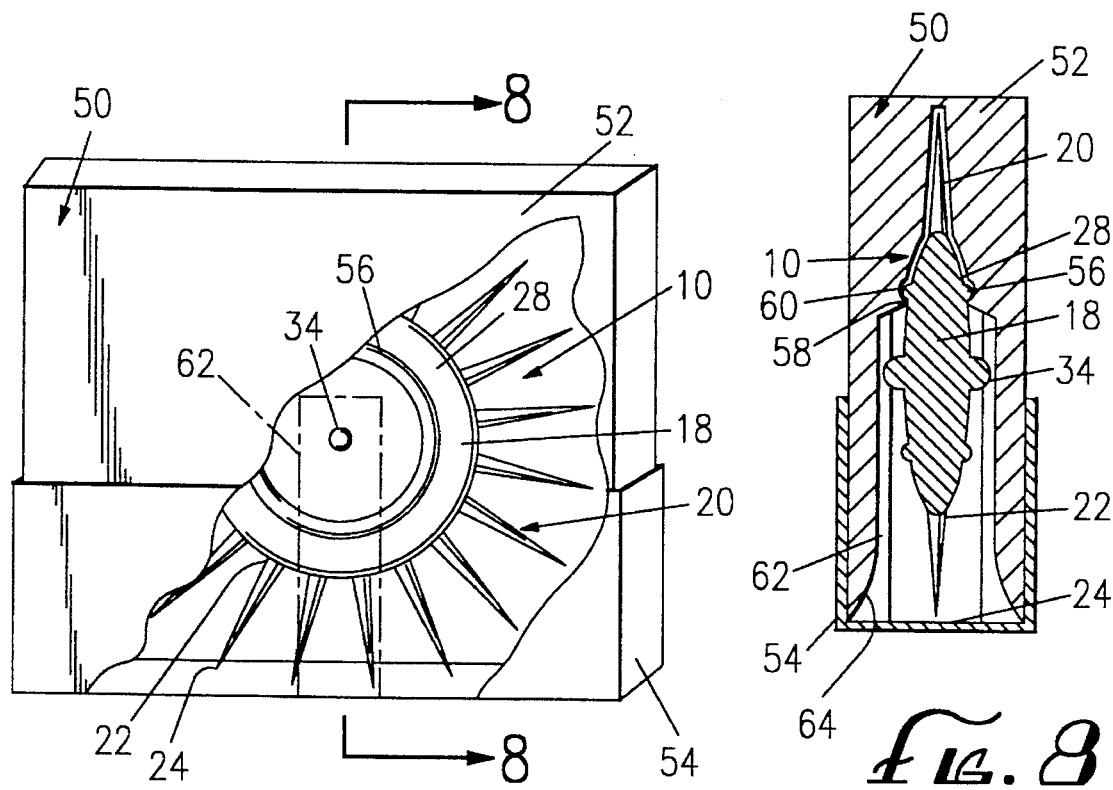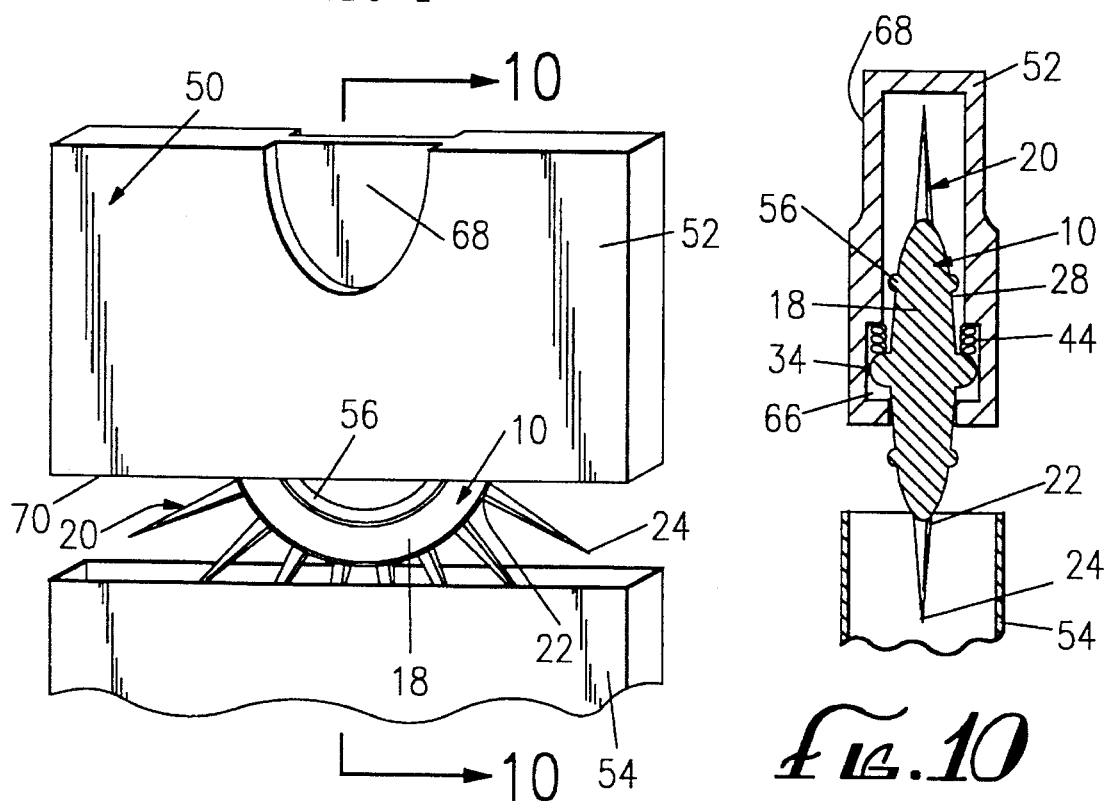

UNIFORM PRESSURE DIAGNOSTIC PINWHEEL

BACKGROUND

This is a continuation in part of application Ser. No. 08/023,593 filed Feb. 26, 1993 now U.S. Pat. No. 5,433,212. The present invention relates to the field of hand-held diagnostic tools used to determine whether humans can distinguish between the sensations of pressure and sharpness.

The device currently used by orthopedists, neurologists, neurosurgeons, and other physicians to test a patient's ability to feel sharp contact with the skin, and so determine a patient's pain threshold as a test for nerve damage, or nerve dysfunction, consists of a pinwheel rotatably attached to a handle. This device traditionally has metal spokes extending from the hub, each spoke being sharpened on its exposed end to produce a sensation of sharpness or discomfort when rolled over a patient's skin. In the clinical setting, the examiner holds the handle and rolls the pinwheel over the patient's extremity or trunk with the pointed ends of the spokes in contact with the patient's skin while the examiner asks the patient whether the sensation produced is sharp or dull.

All pressure applied by the physician or examiner to the handle is transferred directly to the patient's skin through the pinwheel. As a result it is difficult to control the force applied to the patient's skin or to compare the results of tests performed by more than one physician.

It is almost impossible to effect an accurate diagnosis using this type of pinwheel without the possibility of piercing a patient's skin. Additionally, the same device is routinely used to examine many different patients, and is often not sterilized after each testing procedure. Once it pierces a patient's skin, the spokes of the pinwheel become contaminated by that patient's body fluids and can be a source of cross-contamination. Because of A.I.D.S. and other deadly diseases that can be transmitted through body fluids, both the examiner and other patients tested with the contaminated pinwheel are put at high risk of infection through contact with this type of pinwheel.

Although making the pinwheel's spokes less sharp decreases the chances that they will pierce skin, this also decreases the patient response and thus the accuracy of an examination as the patient senses pressure rather than sharpness. Examination accuracy and safety is further complicated by the fact that skin on different body parts has differing thicknesses and sensitivities; while light pressure may elicit the sensation of sharpness on one part of a patient's body, additional pressure is required on others. Heretofore, the examiner has been solely responsible for providing the proper pressure to elicit a sharp sensation while avoiding piercing a patient's skin.

Besides the possibility of cross-contamination, continued reuse of current devices can result in a dulling of the spokes' points over time, thus reducing the effectiveness of the reusable pinwheel as a diagnostic tool. Additionally, in an attempt to address the contamination issue, some physicians have sterilized the pinwheel devices. Repeated sterilization also contributes to a loss in sharpness.

Physicians have recognized the dangers to their patients and to themselves of using a necessarily sharp and potentially contaminated device for examinations, but have heretofore failed to successfully solve these problems. As an alternative to the traditionally used metal pinwheel, some physicians currently use either a hypodermic needle or a safety pin to test sharpness sensation in patients, since both of these may be disposed of after use. However, hypodermic needles are especially designed to minimize pain on insertion through the skin, and this design is not effective in diagnostic sensation testing. Safety pins are not sterile, and if they pierce the skin can infect the patient. Further, both hypodermic needles and safety pins have only one sharp point, and to test the surface of a patient's skin requires repeated and time consuming poking of the skin in multiple places with varying degrees of pressure to test the patient's ability to sense sharpness.

There is therefore a need to provide a diagnostic device to test a patient's ability to sense sharpness under a more controllable pressure while also protecting both patient and physician from the risk of acquiring communicable diseases through transmission of body fluids.

SUMMARY

The instant device solves these problems by providing a constant pressure diagnostic device having a pinwheel head that may be used for a single patient and then thrown away, or removed and sterilized between each use.

A device incorporating features of the present invention comprises a pinwheel having spokes extending from a hub, each spoke having a pointed end, and a shock absorbing means to dampen the force applied to the pinwheel head by the examiner so that the chance of piercing the patient's skin during examination is reduced. Further, since differing pressures are usually needed on differing sites on a patient's skin to elicit a sensation of sharpness, devices with controlled but different levels of "shock absorption" may be used. The physician may therefore use one pinwheel on sensitive skin, and a second on tougher skin, with each pinwheel having a differently calibrated "shock absorber" effecting a different pressure.

Further, the device can provide for a detachable pinwheel head which may either be disposed of, or may be fully sterilized after each use. Each pinwheel head has a means for gripping the pinwheel head safely to detach it without danger of contamination.

Still further, the device provides for a cover which shields the examiner from contact with the sharp spokes of the pinwheel head until the cover is removed to allow use, and which cover also prevents contamination of the pinwheel head during transportation of the device.

DRAWINGS

These and other features, aspects and advantages of the present invention will become better understood with reference to the following description, appended claims, and accompanying drawings, where:

FIG. 3 is a side view of the pinwheel of FIG. 1.

FIG. 4 is a cross sectional view of the pinwheel of FIG. 3 taken along line 4—4 of FIG. 3.

FIG. 5 is a side view of a second version of the pinwheel of FIG. 1.

FIG. 6 is a cross sectional view of the pinwheel of FIG. 5 taken along line 5—5 of FIG. 5.

FIG. 7 is a partially cutaway side view of the pinwheel of FIG. 3 enclosed in a carrying box.

FIG. 8 is a cross sectional view of the pinwheel and carrying box of FIG. 7 taken along line 8—8 of FIG. 7.

FIG. 9 is an exploded side view of the pinwheel of FIG. 3 in a second version of the carrying box.

FIG. 10 is a cross sectional view of the pinwheel and carrying box of FIG. 9 taken along line 10—10 of FIG. 9.

DESCRIPTION

Figure 1:
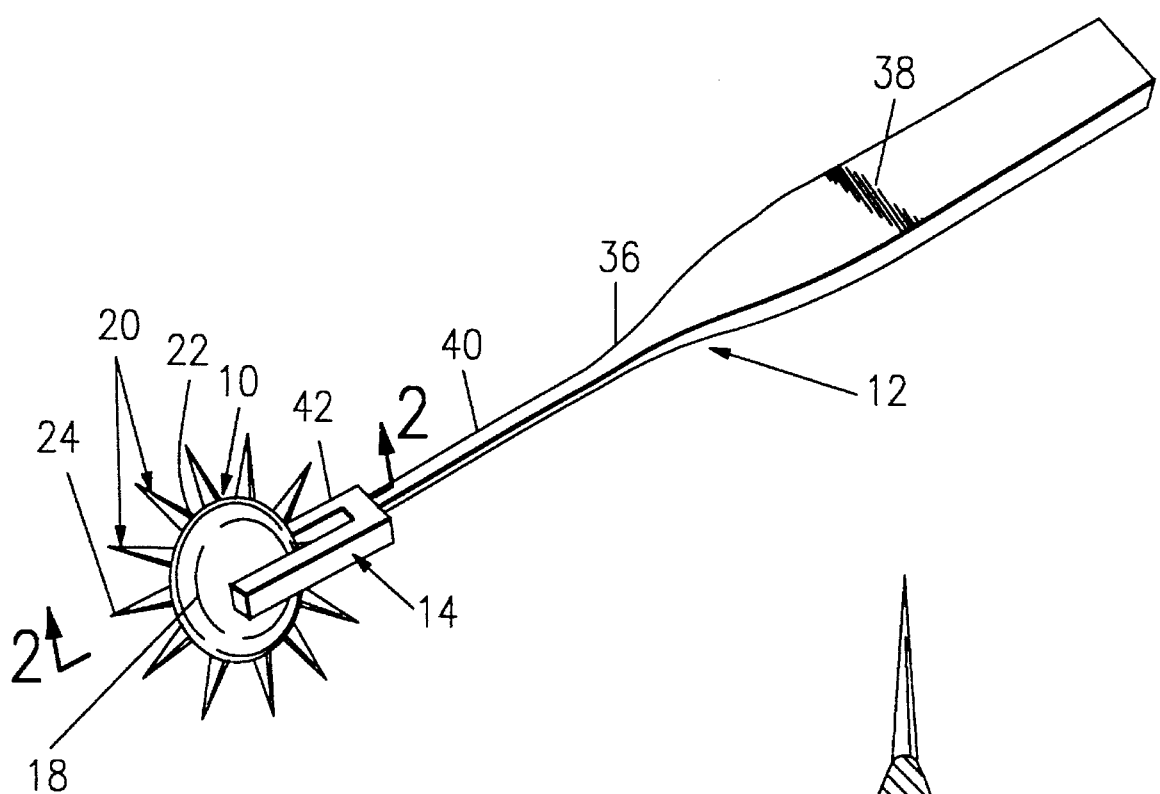
FIG. 1 is a perspective side view showing a diagnostic pinwheel embodying features of the invention.
Figure 2:
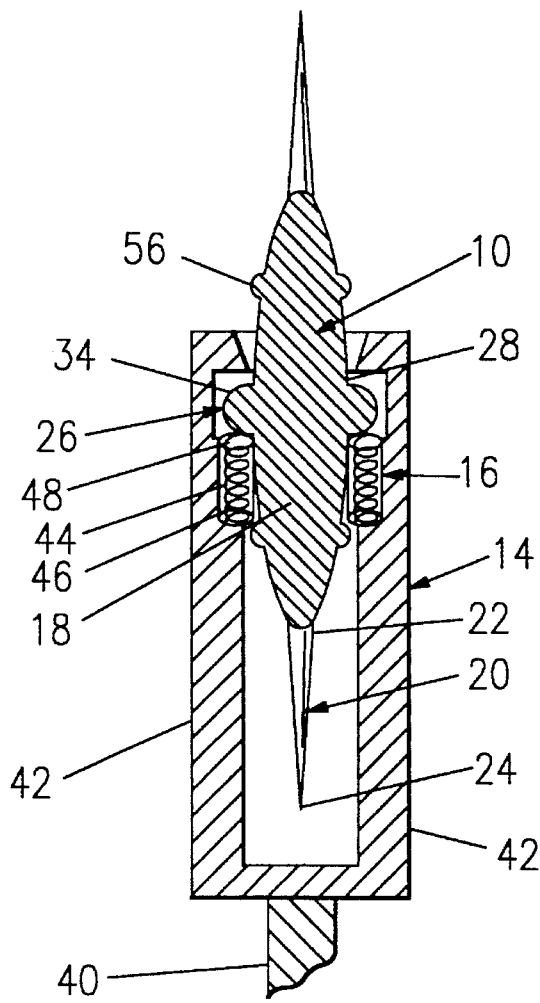
FIG. 2 is a cross sectional view of the head portion of the diagnostic pinwheel of FIG. 1 taken along line 1—1 of FIG. 1.

FIG. 1 shows a device embodying features of the invention to test the nerve response by the sensation of sharpness in humans. The device comprises a pinwheel 10, a grasping means 12 with a mounting head 14 for the pinwheel 10, and force absorption means 16. FIG. 2 is an enlarged view of the pinwheel 10 and mounting head 14 of FIG. 1 showing a first variant of the device embodying the invention.

The pinwheel 10 comprises a hub 18 and a plurality of spokes 20 extending radially from the perimeter of the hub 18. While a circular cross section is preferred for the hub 18 any cross section may be used. Each spoke 20 has a first end 22 attached to the perimeter of the hub 18 and a second end 24 distal to the hub 18. A cross section of each spoke 20 may define, but is not limited to defining, a circle. Each spoke second end 24 is configured to create a sensation of discomfort different than pressure, such as a feeling of sharpness, in a patient when the spoke second end 24 is pressed against the patient's skin. This is accomplished by forming a point having a diameter of as small as is practicable. The hub is typically from about 1 to about 3 centimeters in diameter and typically about 2 centimeters and about 0.5 centimeters thick. The first end 22 of each spoke 20 is typically from about 0.1 to about 0.5 centimeters, preferably about 0.75 centimeters in diameter. Each spoke is typically about 0.5 to about 1.5 centimeters, preferably about 1.0 centimeters in length. As a result the hub and spoke combination may have a diameter of from about 2 centimeters to about 6 centimeters.

The hub 18 of the pinwheel 10 has an axis extending through the center thereof perpendicular to the plane of the spokes 20. An attachment means is located along the axis, the attachment means being equally spaced from each spoke second end 24 and perpendicular to the spokes 20. The attachment means can extend either along the axis either into the hub 18, or outward away from the surface 28 of the hub 18 as shown in FIGS. 5 and 6. If the attachment means 26 extends inward, it typically is a circular hole 30 extending below the surface 28 of the hub 18. In such an instance, the hub 18 also has a groove 32 along the surface 28 of the hub 18 to allow a protrusion in the handle (not shown) to rest in the hole. If the attachment means 26 extends outward, it is an axle 34 extending above the hub surface 28. If the attachment means 26 extends inward, it may extend through the thickness of the hub 18, and has a diameter at the surface 28 of the hub 18 of from about 0.05 to about 0.2 centimeters. If an axle 34 extends outward, it typically extends from about 0.1 to about 0.3 centimeters outward, and has a diameter at the surface 28 of the hub 18 of from about 0.05 to about 0.2 centimeters.

The attachment means 26 on the hub 18 is connected to the grasping means 12 by the mounting head 14 so that the pinwheel 10 is free to rotate around its axis. In a first embodiment, the grasping means 12 can be a handle 36 comprising a grip 38, and a neck 40 which terminates in the mounting head 14. The mounting head 14 can be a single arm (not shown) or a bifurcated head consisting of two arms as shown in FIG. 1. The mounting head 14 is configured to allow the pinwheel 10 to rotate freely between the arms 42 about the attachment means 26 without the hub 18 or the spokes 20 contacting the mounting head 14. The grip 38 is configured to fit comfortably in a human hand and is typically between about 4 to about 10 centimeters long and between about 0.5 to about 2.0 centimeters thick. The neck 40 which provides a flexible connection between the grip 38 and the mounting head 14, is typically between about 3 to about 9, preferably about 6 centimeters long and between about 0.25 to about 0.75 centimeters thick.

The grasping means 12 can include a force absorption means which dampens force applied to the pinwheel 10 through the grasping means 12. This force absorption means can be a pliable handle 36 or pliable neck 40 that is calibrated to dampen the force applied to the pinwheel 10 through the handle 36. Alternatively, the force absorbing means can be a mechanical bending means incorporated in the handle 36 or one or more force absorbing members 44 each having a first end 46 fixedly attached to the mounting head 14, and a second end 48 urged against the attachment means 26. Such force absorbing members are typically springs made of either metal or plastic with memory such as shown in FIG. 2 which are capable of absorbing forces normally applied during testing procedures. Such force absorbing members absorb force directed pinwheel 10 when the axis of the grasping means is approximately perpendicular to the surface of the skin being tested.

Alternatively, the force absorbing means may comprise a ring made of force absorbing material that maintains its physical properties through repeated heat or chemical sterilization. This ring is fixed in the mounting head 14 if the pinwheel's attachment means 26 extend outward from the pinwheel, and this ring is fixed in the pinwheel 10 if the pinwheel's attachment means 26 extend inward. In either configuration, the inner diameter of the ring is from about 0.05 to about 0.2 cm., depending on the diameter of the attachment means 26, and in any event is large enough to permit the attachment means 26 free rotation about its axis when the pinwheel 10 is mounted on the mounting head 14. This ring acts to absorb force applied through the grasping means 12 directed toward the pinwheel along a plane defined by the grasping means and the plane defined by the pinwheel's spokes.

FIGS. 7 and 8 show a detachable carrying box 50 which encloses the pinwheel 10 and protects the second ends 24 of the spokes 20 from being damaged or users from being injured by the sharp spokes 20. The sealed carrying box 50 also maintains sterility of the pinwheel 10. In the embodiment of FIGS. 7 and 8, the detachable carrying box 50 is configured to snugly fit over the spokes 20 of the pinwheel 10, yet allow for easy removal or replacement.

The carrying box 50 of FIGS. 7 and 8 includes and upper cover 52 and a cap 54 which fits on to the upper cover 52. The combination of upper cover 52 and cap 54 encloses the pinwheel 10. To aid in holding the pinwheel 10 in the upper cover 52 the pinwheel 10 has a raised ring 56 which can be pushed past the ridge 58 on the inner surface of the upper cover 52 so that it rests in groove 60, thus holding the pinwheel 10 in the upper cover 52 until the pinwheel 10 is attached to the handle 36. Alternatively, in an embodiment not illustrated, to aid in holding the pinwheel 10 in the upper cover 52 the pinwheel has a groove at the same location and instead of the raised ring 56, which groove is configured to receive a raised ridge. Corresponding to this groove is a raised ridge, which ridge is in substantially the same location and which takes the place of the groove 60 on the inner surface of the upper cover 52 so that the raised ridge rests in the pinwheel's groove, thus holding the pinwheel 10 in the upper cover 52 until the pinwheel 10 is attached to the handle 56. To simplify attachment of the covered pinwheel 10 onto the handle 36 the upper cover 52 can include a channel 62 which approximates the width of the mounting head 14 and thus acts as a guide for insertion of the handle 36. Additionally, the lower portion of the upper cover 52 can include beveled edges 64 so that upon insertion of the mounting head 14 into the channel 62 the sides of the upper cover 52 spread slightly allowing the ring 56 to be released from the groove 60 as the axle 34 lodges within the mounting head 14.

To use the pinwheel 10 as shown in FIGS. 1–8 the cap 54 is removed from the upper cover 52, and the mounting head 14 is inserted into the upper cover 52 using the channel 62 as a guide. The mounting head 14 is advanced until the axle 34 is lodged in a matching indentation in the head 14. The pinwheel 10, now attached to the handle 36 can be removed from the cover 52 and used in the normal manner. However, because of the predesigned force absorbing nature of the handle 36 or the inclusion of the force absorbing member 44, the physician, nurse or technician has more control over the application of force to the patient. After use the pinwheel 10 can be removed from the mounting head 14 and disposed of so that cross contamination can not occur.

FIGS. 9 through 13 show variations of the pinwheel 10 which do not require a separate handle as the carrying box 50 acts as the grasping means 13. FIGS. 9 and 10 shows at least half of a pinwheel 10 enclosed within the upper cover 52 with the axle 34 caged in hole 66 which acts as a bearing for the axle 34. The cover can also be constructed with axle like protrusions (not shown) located on the inner surface of the cover in place of the hole 66. The protrusions then set into the circular hole 30 shown in FIG. 6 to hold the pinwheel 10 within the upper cover 52. The upper portion of the upper cover 52 can also include a finger grip 68 to aid in grasping the upper cover 52 when diagnostic tests are performed. FIG. 9 shows the finger grip 68 along the vertical axis which passes through the hole 66 of the upper cover 52. However, improved control of diagnostic technique may be obtained if the finger grip 68 is placed at an angle to the vertical. The exposed portion of the pinwheel 10 is enclosed by the addition of the closed end cap 54 which is placed over the open end of the upper cover 52 in the same manner as shown in FIGS. 7 and 8. To additionally assure maintenance of sterility of the unused pinwheel 10 the juncture between the upper cover 52 and the cap 54 can be sealed by a tape (not shown) wrapped around the outside of the assembly. As a further modification, the upper cover 52 may include force absorbing members 44 such as springs to aid in controlling the force applied to the patient's skin during use of the pinwheel 10.

Figure 12:
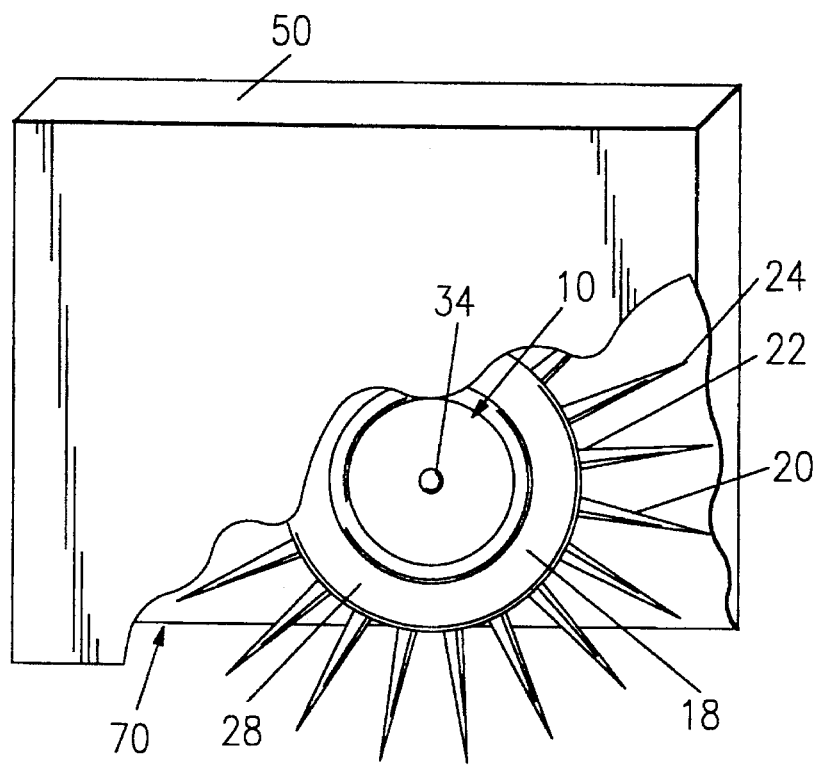
FIG. 12 is a partially cut away side view of the third version of the pinwheel and carrying box of FIG. 9 showing the pinwheel in its diagnostic position.
Figure 11:
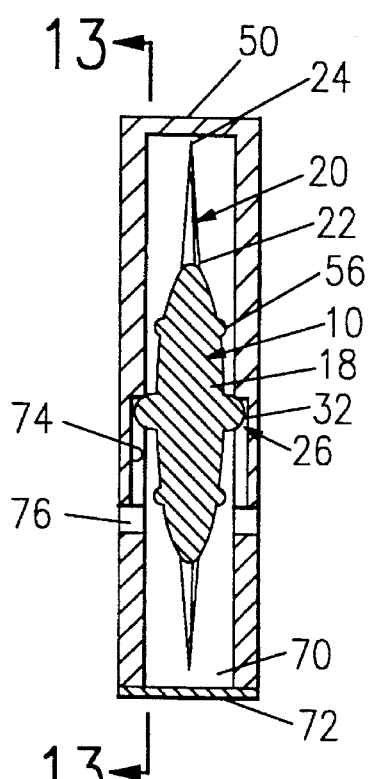
FIG. 11 is a cross sectional view of a third version of the pinwheel and carrying box of FIG. 7 taken along line 8—8 of FIG. 7.
Figure 13:
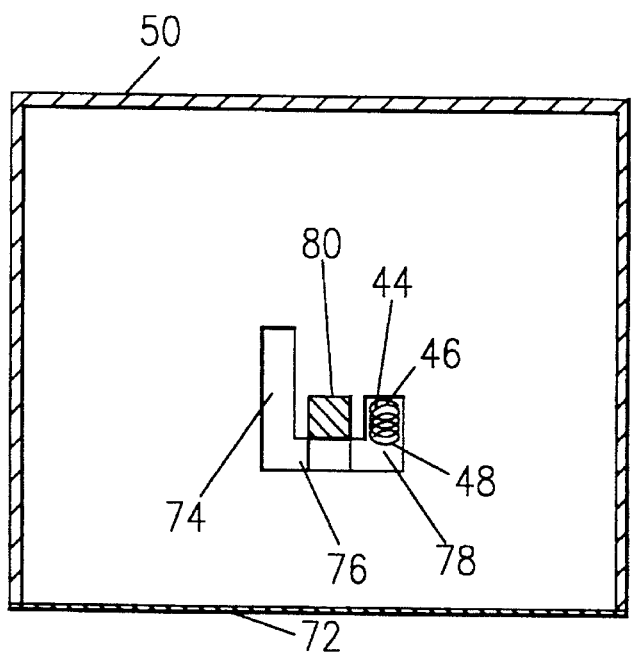
FIG. 13 is a front view of the interior surface of a wall of the carrying box.

FIGS. 11 through 13 show a still further version of the pinwheel 10 and carrying box 50. In its unused position the pinwheel 10 is completely enclosed by a carrying box 50 having a single open end 70. FIG. 11 shows the pinwheel 10 in its stored position in the center of the carrying box 50 with a sealing tape 72 across the open end 70. As best shown in FIG. 13, the inner surfaces of the carrying box 50 includes a vertical groove 74, a horizontal groove 76 and a locking channel 78, all interconnecting. The locking channel 78 may also include a force absorbing member 44 to absorb pressure applied during use. A finger grip 68 may also be added.

To use the embodiment of FIGS. 9–10 the operator only has to remove the cap 54, grasp the upper cover 52 by the finger grip 68 and apply the spokes 20 of the pinwheel 10 to the patient's skin. The bearing surface built into the upper cover 52 allows the pinwheel 10 to freely rotate and the force absorbing members 44 allow control of the applied pressure. The pinwheel 10 can then be readily disposed of without fear of injury or cross contamination by reapplying the cap 54.

To use the embodiment of the pinwheel 10 and cover of FIGS. 11–13 the pinwheel 10 is moved from its rest storage position in the center of the carrying box 50 to (FIG. 11) to its operable position (FIG. 12) by sliding axle 34 along the vertical groove 74 and the horizontal groove 76 until it is resting in the locking channel 78 and in contact with the force absorbing member 44. To aid in retaining the pinwheel 10 in its operable position a locking pin 80 can be positioned in the horizontal channel 76.

Figure 14:
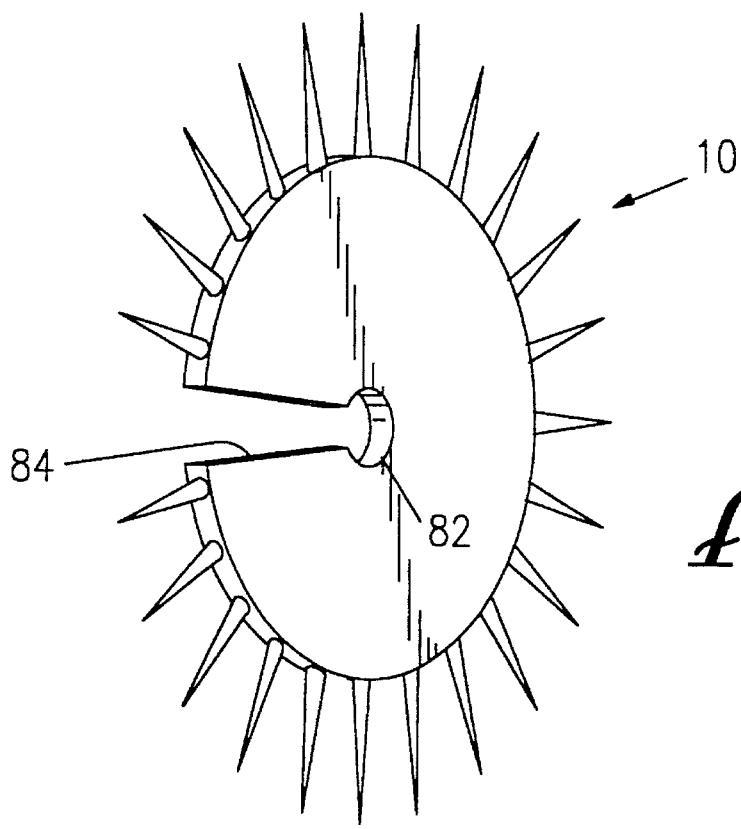
FIG. 14 is a side view of a pinwheel with a slot extending from a hole along the pinwheel's axis to perimeter of the pinwheel.
Figure 15:
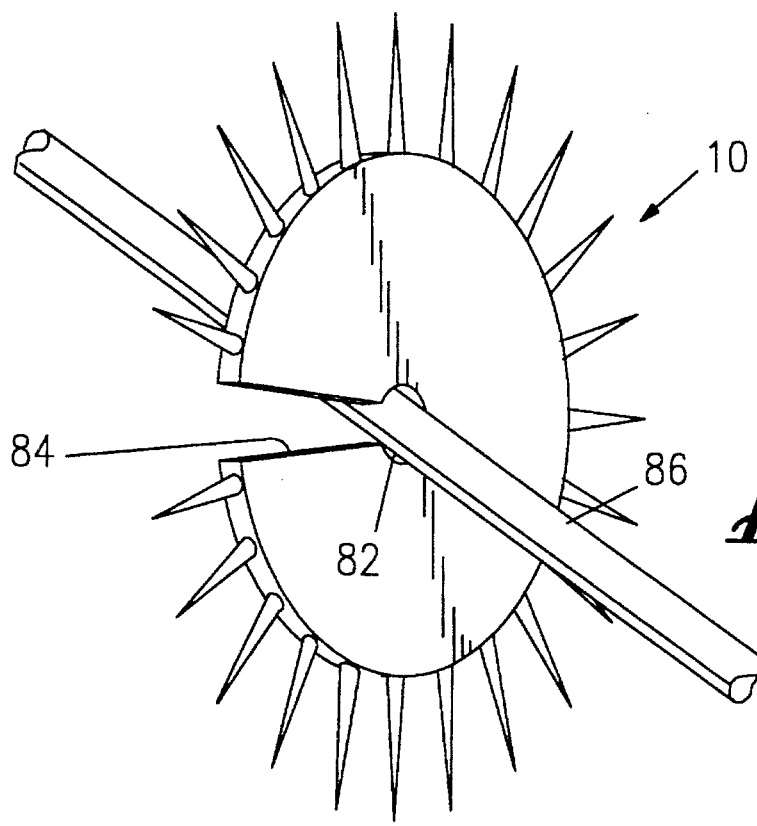
FIG. 15 is side view of a pinwheel with a slot extending from a hole along the pinwheel's axis to the perimeter of the pinwheel mounted on an axle.

FIGS. 14 and 15 are side views of an additional embodiment of the pinwheel 10 in which the attachment means 26 is a hole 82 along the axis of the pinwheel 10. Leading from the hole 82 is a slot which extends to the perimeter of the pinwheel. The slot 84 is adapted to receive a pinwheel supporting axle 86 permanently mounted onto the grasping means 12, the slot being narrower at the point of intersection with the hole than the diameter of the supporting axle 86.

To insert the axle 86 into the hole 82, the axle 86 is placed in the slot 84 at the perimeter and forced along the slot 84 until it encounters resistance at the narrow portion. Further pressure forces the two edges of the narrow portion to be temporarily displaced, thereby widening the gap between the two edges and allowing placement of the axle 86 in the hole 82 and along the axis. The pinwheel 10 is removed from the axle 86 by pressing the axle 86 against the two edges of the narrow portion of the slot 84 to displace them temporarily and then sliding the axle 86 along the slot 82 to the perimeter of the pinwheel 10.

The design of the pinwheel 10 and the various grasping means 12 allows fabrication from several relatively inexpensive polymers and reinforced plastics such as nylons, acrylics, polycarbonates, or metals such as stainless steel or titanium. These materials can be formed into sharply pointed spokes 20 with minimal problems of breakage or dulling under normal use conditions. If a standard type handle 36 is used, standard materials, such as stainless steel or high strength polymeric composites are suitable as the handle 36 is reused while the pinwheel 10 is disposed of after each use.

The cover may be of the same or similar materials, as well as other common materials used to construct disposable medical devices such as polyethylene, polypropylene and other relatively stiff plastic materials which can formed into a protective but graspable structure. The use of these materials allows for inexpensive fabrication and sterilization of the pinwheel and cover. As a result the product can be used once and then disposed of to avoid cross-contamination and the time and expense of resterilization. Even if reused, the cover protects the operator from injury resulting from carrying the sharp pointed pinwheel. While the dimensions listed above are representative of current reusable pinwheel products, these dimensions should be considered to limit the dimensions of the disposable self-contained products such as shown in FIGS. 9–13. For ease of use, the self-contained product may have a pinwheel with a radius 2 to 3 times that of current reusable units, the primary constraining factor being that the sharpness of the second end of the spoke must be retained. The cover is then appropriately sized to enclose the pinwheel without damaging the sharp end of the spokes.

Although the present invention has been described in considerable detail with reference to certain preferred versions and uses thereof, other versions and uses are possible. For example, the pinwheel can be adapted to mount on other currently used handles including, for example, the handle end of the a reflex hammer. Also features of one embodiment can be incorporated in the other versions. Each of the variations can utilize the pinwheel design shown in FIG. 6 rather than the structure of FIG. 4. Therefore, the spirit and scope of the appended claims should not be limited to the description of the preferred versions contained herein.

What is claimed is:

1. A device for testing for nerve dysfunction comprising a pinwheel, a grasping means for the pinwheel, and force absorption means whereby
   a. the pinwheel comprises a hub, a plurality of spokes extending radially from the perimeter of the hub, and attachment means centrally located in the hub for connecting the pinwheel to the grasping means, i) each spoke having a first end attached to the perimeter of the hub and a second end distal to the hub whereby each second end is configured to create a sensation of discomfort when the second end is pressed against human skin, and ii) an axis through the attachment means being equally spaced from each spoke's second end and perpendicular to the spokes;
   b. the grasping means holding the attachment means while allowing the pinwheel to freely rotate; and
   c. the force absorption means being positioned to dampen forces applied to the pinwheel through the grasping means, whereby the grasping means comprises an axle and the attachment means comprises a hole along the axis of the pinwheel, a slot extending from the hole to the perimeter of the pinwheel, said slot having a narrow portion at its intersection with the hole, said narrow portion being smaller than the diameter of the axle, while allowing the axle to be pushed through the slot and then into the hole to mount the pinwheel on the axle.

2. A device according to claim 1 whereby the grasping means is a handle.

3. A device according to claim 1 whereby the force absorption means comprises a pliable handle.

4. A device according to claim 1 whereby the force absorption means comprises one or more force absorbing members, each force absorbing member being located between the attachment means and the grasping means.

5. A device according to claim 1 such that the grasping means is a handle which comprises a grip, a neck attached to the grip and a bifurcated head mounted on the end of the neck, the grip being configured to fit comfortably in a human hand, and the bifurcated head having two extending arms and being configured to receive and grasp the attachment means between the arms and allow the pinwheel head to rotate freely between the arms.

6. The device of claim 1 further including a cover which removably attaches to the device so that the second end of the spokes are not accessible unless the cover is removed.

7. The device of claim 1 wherein the grasping means is a cover which at least partially surrounds the pinwheel, the attachment means being connected to the cover so that the pinwheel is free to rotate, about the axis through the attachment means and at least the second end of one or more of the spokes is not covered by the cover.

8. A device according to claim 2 whereby the force absorption means comprises one or more force absorbing members, each force absorbing member having a first end fixedly attached to the handle, and a second end proximate to one or more of the hub's attachment means.

9. The device of claim 7 further including a closure which cooperates with the cover to totally surround the pinwheel.

10. The device of claim 7 wherein the attachment means is positionable within the cover in either a first or a second location such that the cover fully surrounds the pinwheel when positioned in the first location and the cover only partially surrounds the pinwheel in the second location so that the second end of one or more spokes can be brought in contact with a patient's skin.

11. The device of claim 7 wherein the force absorption means is positioned between the cover and the attachment means.

12. The device of claim 9 wherein the cover has an open end allowing access to the second end of at least some of the spokes and the closure is a tape secured over the open end.

13. The device of claim 9 wherein the cover has an open end allowing access to the second end of at least some of the spokes and the closure is a cap which connects to the cover.

14. A pinwheel for testing tactile sensations and a carrier for the pinwheel wherein
   a. the pinwheel comprises a hub and spokes radiating from the hub, the hub having an axis through the center thereof and attachment means located along the axis, each spoke having a sharpened end spaced from the hub, the sharpened end capable of creating a sensation of pain when pressed against the skin of a responsive organism, and
   b. the carrier comprises a cover which at least partially surrounds the pinwheel, the cover having therein means to hold the pinwheel within the cover until such time as removal from the cover is desired, whereby the means to hold the pinwheel comprises an axle, and the attachment means comprises a hole along the axis of the pinwheel, the pinwheel having a slot extending from the hole to the perimeter of the pinwheel, said slot having a narrow portion at its intersection with the hole, which narrow portion is smaller than the diameter of the axle, such that when the axle is pushed through the slot and then into the hole to mount the pinwheel on the axle the axle remains in the hole until forceably removed.

15. The device of claim 14 wherein the cover includes guiding means for receiving a handle designed to mate with the attachment means.

16. The device of claim 14 wherein the cover includes means to mate with the attachment means such that when the attachment means is mated with the cover the pinwheel is free to rotate about its axis, and each successive spoke second end extends beyond the cover as the pinwheel is rotated.

17. The device of claim 14 further including closure means which cooperates with the cover to completely enclose the pinwheel.

* * * * *